United States Patent
Dodo et al.

(10) Patent No.: US 9,670,459 B2
(45) Date of Patent: Jun. 6, 2017

(54) PRODUCTION METHOD FOR CELL POPULATIONS

(75) Inventors: Katsuyuki Dodo, Otsu (JP); Hideto Chono, Otsu (JP); Junichi Mineno, Otsu (JP)

(73) Assignee: TAKARA BIO INC., Shiga (JP)

( * ) Notice: Subject to any disclaimer, the term of this patent is extended or adjusted under 35 U.S.C. 154(b) by 137 days.

(21) Appl. No.: 13/816,001

(22) PCT Filed: Aug. 9, 2011

(86) PCT No.: PCT/JP2011/068153
§ 371 (c)(1),
(2), (4) Date: Feb. 8, 2013

(87) PCT Pub. No.: WO2012/020757
PCT Pub. Date: Feb. 16, 2012

(65) Prior Publication Data
US 2013/0142766 A1    Jun. 6, 2013

(30) Foreign Application Priority Data

Aug. 10, 2010  (JP) ................................ 2010-179702

(51) Int. Cl.
| | |
|---|---|
| *A61K 38/00* | (2006.01) |
| *C12N 5/00* | (2006.01) |
| *C12N 5/18* | (2006.01) |
| *C12N 5/0783* | (2010.01) |
| *A61K 35/17* | (2015.01) |
| *A61K 35/12* | (2015.01) |

(52) U.S. Cl.
CPC ............ *C12N 5/0636* (2013.01); *A61K 35/17* (2013.01); *C12N 5/0637* (2013.01); *A61K 35/12* (2013.01); *C12N 2501/2304* (2013.01); *C12N 2501/998* (2013.01); *C12N 2510/00* (2013.01)

(58) Field of Classification Search
None
See application file for complete search history.

(56) References Cited

U.S. PATENT DOCUMENTS

| 2005/0042208 A1* | 2/2005 | Sagawa et al. .............. 424/93.7 |
| 2008/0019948 A1 | 1/2008 | Nishimura et al. |

FOREIGN PATENT DOCUMENTS

| JP | 2005-179299 | | 7/2005 |
| WO | WO 2007020880 | * | 2/2007 |
| WO | 2008/143255 | | 11/2008 |
| WO | WO2008143255 | * | 11/2008 |
| WO | WO2009151183 | * | 12/2009 |

OTHER PUBLICATIONS

Germann et al ( Immunobiology, 1996, v.196, pp. 475-484).*
International Search Report issued Sep. 13, 2011 in International (PCT) Application No. PCT/JP2011/068153.
M. Oyoshi et al., "TRAF1 controls the Th2 differentiation of T cells limiting NIP45 nuclear translocation", FASEB Journal, vol. 19, No. 5, Suppl. S, Part 2, p. A1448, Section 827.3, 2005.
L. Wei et al., "IL-21 is Produced by Th17 Cells and Drives IL-17 Production in a STAT3-dependent Manner", The Journal of Biological Chemistry, vol. 282, No. 48, pp. 34605-34610, 2007.
S. Ferrari-Lacraz et al., "IL-21 promotes survival and maintains a naive phenotype in human $CD4^+T$ lymphocytes", International Immunology, vol. 20, No. 8, pp. 1009-1018, 2008.
V. Oliveira et al., "Anti-CD4-mediated selection of Treg in vitro-in vitro suppression does not predict in vivo capacity to prevent graft rejection", Eur. J. Immunol., vol. 38, pp. 1677-1688, 2008.
A. Aruga et al., "Enhancement of In Vitro Cytolytic Reactivity of T Cells Stimulated with Tumor-Pulsed Dendritic Cells", Biotherapy, vol. 12, No. 5, pp. 875-877, 1998.
R. Kemp et al., "The phenotype of type 1 and type 2 $CD8^+T$ cells activated in vitro is affected by culture conditions and correlates with effector activity", Immunology, vol. 115, pp. 315-324, 2005.
K. Chamoto et al., "An Essential Role of Antigen-Presenting Cell/T-Helper Type 1 Cell-Cell Interactions in Draining Lymph Node during Complete Eradication of Class II-Negative Tumor Tissue by T-Helper Type 1 Cell Therapy", Cancer Research, vol. 66, No. 3, pp. 1809-1817, 2006.
J. Rossi et al., "Genetic therapies against HIV", Nature Biotechnology, vol. 25, No. 12, pp. 1444-1454, 2007.
International Preliminary Report on Patentability and Written Opinion issued Mar. 12, 2013 in International (PCT) Application No. PCT/JP2011/068153.

* cited by examiner

*Primary Examiner* — Michail Belyavskyi
(74) *Attorney, Agent, or Firm* — Wenderoth, Lind & Ponack, L.L.P.

(57) ABSTRACT

The present invention addresses the problem of providing cell populations having a high proportion of CD4-positive naive T cells and/or CD4-positive central memory T cells, and a production method thereof. The present invention provides a production method for CD4-positive T cell populations which is characterized by using anti-CD3 antibodies, fibronectin fragments, and Interleukin-4. The method is characterized not only by the attainment of a cell group with a high proportion of CD4-positive naive T cells and/or CD4-positive central memory T cells, but also by a high bulk yield.

6 Claims, No Drawings

SEQUENCE LISTING

```
<160> NUMBER OF SEQ ID NOS: 9

<210> SEQ ID NO 1
<211> LENGTH: 25
<212> TYPE: PRT
<213> ORGANISM: Artificial Sequence
<220> FEATURE:
<223> OTHER INFORMATION: partial region of fibronectin named CS-1
```

<400> SEQUENCE: 1

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 2
<211> LENGTH: 94
<212> TYPE: PRT
<213> ORGANISM: Artificial Sequence
<220> FEATURE:
<223> OTHER INFORMATION: partial region of fibronectin named III-10

<400> SEQUENCE: 2

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 3
<211> LENGTH: 4
<212> TYPE: PRT
<213> ORGANISM: Artificial Sequence
<220> FEATURE:
<223> OTHER INFORMATION: partial region of fibronectin named RGDS

<400> SEQUENCE: 3

Arg Gly Asp Ser
1

<210> SEQ ID NO 4
<211> LENGTH: 274
<212> TYPE: PRT
<213> ORGANISM: Artificial Sequence
<220> FEATURE:
<223> OTHER INFORMATION: fibronectin fragment named C-274

<400> SEQUENCE: 4

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro

```
            100                 105                 110
Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
            165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp

<210> SEQ ID NO 5
<211> LENGTH: 271
<212> TYPE: PRT
<213> ORGANISM: Artificial Sequence
<220> FEATURE:
<223> OTHER INFORMATION: fibronectin fragment named H-271

<400> SEQUENCE: 5

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
            35                  40                  45

Asn Leu Ala Pro Asp Ser Ser Ser Val Val Val Ser Gly Leu Met Val
            50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
            85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
            115                 120                 125

Val Pro Ala Asn Gly Gln Thr Pro Ile Gln Arg Thr Ile Lys Pro Asp
            130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
            165                 170                 175

Ile Asp Ala Ser Thr Ala Ile Asp Ala Pro Ser Asn Leu Arg Phe Leu
            180                 185                 190
```

```
Ala Thr Thr Pro Asn Ser Leu Leu Val Ser Trp Gln Pro Pro Arg Ala
            195                 200                 205

Arg Ile Thr Gly Tyr Ile Ile Lys Tyr Glu Lys Pro Gly Ser Pro Pro
        210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr
            260                 265                 270

<210> SEQ ID NO 6
<211> LENGTH: 296
<212> TYPE: PRT
<213> ORGANISM: Artificial Sequence
<220> FEATURE:
<223> OTHER INFORMATION: fibronectin fragment named H-296

<400> SEQUENCE: 6

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
    210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr Asp
            260                 265                 270

Glu Leu Pro Gln Leu Val Thr Leu Pro His Pro Asn Leu His Gly Pro
        275                 280                 285
```

```
Glu Ile Leu Asp Val Pro Ser Thr
    290                 295
```

<210> SEQ ID NO 7
<211> LENGTH: 549
<212> TYPE: PRT
<213> ORGANISM: Artificial Sequence
<220> FEATURE:
<223> OTHER INFORMATION: fibronectin fragment named CH-271

<400> SEQUENCE: 7

```
Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350
```

-continued

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
                420                 425                 430

Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr
545

<210> SEQ ID NO 8
<211> LENGTH: 574
<212> TYPE: PRT
<213> ORGANISM: Artificial Sequence
<220> FEATURE:
<223> OTHER INFORMATION: fibronectin fragment named CH-296

<400> SEQUENCE: 8

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

-continued

Ala Leu Asn Gly Arg Glu Glu Ser Pro Leu Ile Gly Gln Gln Ser
            165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
        210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
        290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Val Val
            325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
        370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
            405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
            485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
            515                 520                 525

Ile Tyr Val Ile Ala Leu Lys Asn Asn Gln Lys Ser Glu Pro Leu Ile
        530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
            565                 570

```
<210> SEQ ID NO 9
<211> LENGTH: 302
<212> TYPE: PRT
<213> ORGANISM: Artificial Sequence
<220> FEATURE:
<223> OTHER INFORMATION: fibronectin fragment named C-CS1

<400> SEQUENCE: 9

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Asp Glu Leu Pro Gln Leu Val Thr Leu Pro His
        275                 280                 285

Pro Asn Leu His Gly Pro Glu Ile Leu Asp Val Pro Ser Thr
    290                 295                 300
```

PRODUCTION METHOD FOR CELL POPULATIONS

TECHNICAL FIELD

The present invention relates to a method of producing a cell population useful in the medical field.

BACKGROUND ART

Living organisms are protected from foreign substances mainly by immune responses, and the immune system is made up of various cells and soluble factors produced by them. Among them, a white blood cell, in particular, a lymphocyte plays a central role. The lymphocyte is divided into two major types, B lymphocyte (hereinafter referred to as B-cell) and T lymphocyte (hereinafter referred to as T cell), both of which recognize antigens specifically and act on them to defend the organism.

In the peripheral blood, the majority of T cells are occupied by CD (Cluster of Differentiation) 4-positive T cells having a CD4 marker and CD8-positive T cells having a CD8 marker. The majority of the CD4-positive T cells are called helper T cells (hereinafter referred to as Th cell), which are involved in assistance of antibody production and induction of various immune responses and are classified into Th1 type (Type 1 helper T cell: hereinafter referred to as Th1-type cell) and Th2 type (Type 2 helper T cell: hereinafter referred to as Th2-type cell) depending on different kinds of cytokines produced by antigen stimulation. The majority of CD8-positive T cells are cytotoxic T cells (cytotoxic T-lymphocytes, hereinafter also referred to as CTL) which exhibit cytotoxic activity in response to antigen stimulation.

As the fourth cancer therapy following surgical operations, chemotherapies and radiation therapies, immunotherapies have been recently attracting attention. Since immunotherapies utilize the immunological capability originally possessed by a human, it is said that physical stress on patients is mild as compared with other therapies. Known immunotherapies include therapies comprising transfer of cells such as lymphokine-activated cells, CD4-positive T cells, NKT cells or γδT cells which are obtained by expansion from CTLs induced ex vivo, a peripheral blood mononuclear cell or the like according to various methods; dendritic cell-transferring therapies and peptide vaccine therapies by which induction of an antigen-specific CTL in vivo is expected; Th1-type cell therapies; and an immunological gene therapies comprising transducing genes that can be expected to have various effects into the above-described cells ex vivo and transferring the cells into the body, and the like.

In the immunotherapy, cell therapy using CTLs which have cytotoxic activity has been traditionally provided. However, recently, Th-cell therapy using Th cells which assist the activity of the CTLs attracts attention (for example, Non-patent Literature 1, Patent Literature 1). As described above, Th cells are classified into Th1-type cells and Th2-type cells. The Th1-type cells produce cytokines such as interferon-γ (IFN-γ) and interleukin-2 (IL-2) and serve as an effector of cellular immunity. On the other hand, the Th2-type cells produce cytokines such as IL-4, IL-5, and IL-13 and have a role in regulation of humoral immunity.

As a cell therapy for acquired immune deficiency syndrome (AIDS), a therapy comprising modifying a CD4-positive T cell (for example, by gene transduction) which is the target of HIV viruses, and then transferring the modified cell into a patient recently attracts attention (for example, Non-patent Literature 2). For example, a clinical trial is conducted in the United State wherein the CD4-positive T cell of an HIV patient is transduced with a gene expressing an antisense RNA corresponding to an RNA encoding gp120 which is a structural protein for HIV, and then the CD4-positive T cell having the added anti-HIV effect is transferred into the patient.

In recent years, a naive T cell and a central memory T cell which are in more undifferentiated states attract more attention rather than a Th cell which is a terminally differentiated effector. The naive T cell is a cell (Th0) which has never been activated by an antigen and has not been directed toward differentiation into a Th1-type cell or a Th2-type cell. It has been shown that the differentiation of the naive T cell into a Th1-type cell or a Th2-type cell can be induced by culturing a CD4-positive naive T cell in the presence of an antigen and a cytokine. The naive T cell is known to express cell surface antigen markers of lymphocytes such as CD45RA, CD62L, and CCR7.

As described above, the naive T cell in an undifferentiated stage is important in the fields of cell therapy and gene therapy. For production of a cell population, development of a method comprising a step of producing with high cell growth efficiency a large amount of cells suitable to use in therapy is desired, and thus, a method of producing a Th1-type cell is developed (for example, Patent Literature 2).

CITATION LIST

Patent Literature

Patent Literature 1: JP-A 2005-179299
Patent Literature 2: WO 2008/143255

Non Patent Literature

Non-Patent Literature 1: Cancer Research, Vol. 66, No. 3, pp. 1809-1817 (2006)
Non-Patent Literature 2: Nature Biotechnology, Vol. 25, No. 12, pp. 1444-1454 (2007)

SUMMARY OF INVENTION

Technical Problems

An object of the present invention is to provide a method of producing a cell population effective for cell therapy.

Solution to Problems

As a result of earnest studies to solve the above problems, the present inventors surprisingly found that, when interleukin-4, which was generally used for induction of differentiation into a Th2-type cell, was used together with a CD3 ligand and a fibronectin fragment for expansion of a CD4-positive T cell, the differentiation into a Th2-type cell was not induced and a cell population expressing CD62L and/or CCR7, namely, a cell population containing a high proportion of CD4-positive naive T cells and/or CD4-positive central memory T cells which are more undifferentiated was obtained. Thus, the present invention was completed.

Specifically, the present invention relates to:
[1] A method of producing a cell population expressing CD62L and/or CCR7, the method comprising the following steps:

(1) removing CD8-positive T cells or collecting CD4-positive T cells from a cell population containing T cells; and (2) culturing the cell population obtained by the step (1) in the presence of the following (A) and (B), and for the whole period or a partial period during the culture and/or during expansion after the culture, culturing the cell population in the presence of the following (C):

(A) at least one polypeptide selected from the group consisting of fibronectin, fibronectin fragments and their mixtures, (B) a CD3 ligand, or a CD3 ligand and a CD28 ligand, (C) interleukin-4;

[2] The method according to [1], wherein the step (2) is a step of culturing the cell population in the presence of (A) and (B) and in the presence of (C), and then expanding the obtained cell population in the presence of (C);

[3] The method according to [1], wherein the step (2) is a step of culturing the cell population in the presence of (A) and (B) and in the absence of (C), and then expanding the obtained cell population in the presence of (C);

[4] The method according to [1], wherein the step (2) is a step of culturing the cell population in the presence of (A) and (B) and in the presence of (C), and then expanding the obtained cell population in the absence of (C);

[5] The method according to any one of [1] to [4], further comprising a step for foreign gene transfer;

[6] A cell population obtained by the method according to any one of [1] to [5], which contains a high proportion of at least one kind of cell selected from the group consisting of the following (1) to (5):

(1) a CD4-positive, CD45RA-positive and CCR7-positive T cell, (2) a CD4-positive, CD45RA-positive and CD62L-positive T cell, (3) a CD4-positive, CD45RA-negative and CCR7-positive T cell, (4) a CD4-positive, CD45RA-negative and CD62L-positive T cell, and (5) a CD4-positive and CXCR4-positive T cell; as compared with a cell population obtained by culture in the presence of (A) and (B), or (B), and in the absence of (C);

[7] The cell population according to [6], for use in a medicament;

[8] The cell population according to [6], for use in manufacture of a medicament;

[9] A medicament comprising the cell population according to [6] as an active ingredient; and

[10] A therapeutic or prophylactic method for a disease, comprising a step of administering an effective amount of the cell population according to [6] to a subject.

In the present invention, the term "expansion" means culture for growing a desired cell (culture for increasing the number of a cell).

Effects of Invention

According to the present invention, a method of producing a cell population expressing CD62L and/or CCR7, namely, a cell population containing a high proportion of CD4-positive naive T cells and/or CD4-positive central memory T cells is provided. The method of the present invention has a high cell growth rate. The cell population obtained by the method of the present invention contains a high proportion of CD4-positive, CD45RA-positive and CCR7-positive T cells, CD4-positive, CD45RA-positive and CD62L-positive T cells, CD4-positive, CD45RA-negative and CCR7-positive T cells, CD4-positive, CD45RA-negative and CD62L-positive T cells, or CD4-positive and CXCR4-positive T cells, and is very useful for treating diseases by cell-based immunotherapy.

MODE FOR CARRYING OUT THE INVENTION

In the present invention, the "T cell" is also referred to as a T lymphocyte, and means a cell originating from the thymus gland, among lymphocytes involved in immune response. The T cells include helper T cells (Th1-type cells and Th2-type cells), suppressor T cells, regulatory T cells, CTLs, naive T cells, memory T cells, αβ T cells expressing TCR consisting of an α chain and a β chain, and γδ T cells expressing TCR consisting of a γ chain and a δ chain. Examples of the "cell population containing T cells" used as the starting material of the present invention include blood (peripheral blood, umbilical cord blood, etc.), and bone marrow, as well as cell populations collected, isolated, purified or derived from them which contain peripheral blood mononuclear cells (PBMC), hematopoietic cells, hematopoietic stem cells, umbilical cord blood mononuclear cells, or the like. These cells may have been activated by a cytokine such as IL-2 in vivo or ex vivo. As these cells, those collected from a living organism or those obtained through in vitro cultivation can be used, or they can be also used after cryopreservation.

In the present invention, the "fibronectin (hereinafter, referred to as FN)" and the "FN fragment" may be obtained naturally (native FN, a FN fragment obtained by fragmentation of native FN via enzyme digestion, etc.) or by recombinant DNA technology. FN and a FN fragment can be prepared in a substantially pure form from a naturally occurring material, for example, on the basis of the disclosure by Ruoslahti E. et al., J. Biol. Chem., Vol. 256, No. 14, pp. 7277-7281 (1981). As used herein, the substantially pure FN or FN fragment means that it does not essentially contain other proteins existing together with FN in nature. The FN or FN fragment can be used in the present invention as a single molecule or as a mixture of several kinds of molecules.

Useful information for the FN fragment that can be used in the present invention and preparation of the fragment is available from Kimizuka F., et al., J. Biochem., Vol. 110, pp. 284-291 (1991); Kornblihtt A. R., et al., EMBO J., Vol. 4, No. 7, pp. 1755-1759 (1985); Sekiguchi K., et al., Biochemistry, Vol. 25, No. 17, pp. 4936-4941 (1986), and the like. In addition, a nucleotide sequence encoding FN and an amino acid sequence of FN are disclosed in NCBI Reference Sequence ID (RefSeqID): NM_002026 and NP_002017.

In the present invention, a FN fragment having a cell-adhesive activity and/or a heparin-binding activity can be preferably used. FN has domains having an activity of binding to integrins on the cell surface. Examples of the domain are VLA (very late antigen)-4 and VLA-5 binding domains. At the C-terminal of FN, a region called IIICS exists. The IIICS contains a region consisting of 25 amino acids (SEQ ID NO: 1) which is called CS-1, and the region has an activity of binding to VLA-4.

A repeating sequence called type III is present in FN. The 10th type III repeating sequence (SEQ ID NO: 2) from the N-terminal contains a cell-binding domain. The above-described sequence contains a sequence of 4 amino acids: Arg-Gly-Asp-Ser (RGDS; SEQ ID NO: 3) that plays a central role for binding to VLA-5. C-274 (SEQ ID NO: 4) is a peptide containing the above-described type III repeating sequence (SEQ ID NO: 2) and is one of FN fragments having a strong cell-adhesive activity.

In addition, FN has a heparin-binding activity. A heparin-binding domain of FN corresponds to the 12th-14th type III repeating sequences from the N-terminal. H-271 (SEQ ID NO: 5) is one of recombinant FN fragments which consists of the heparin-binding domain.

In the present invention, FN fragments containing each domain alone, and FN fragments containing two or more domains in which they are linked directly or via a suitable linker can be used. The domains derived from FN contained in the FN fragment may be the same or different from each other. Examples of the FN fragment having two or more binding domains in its molecule include polypeptides such as H-296 (SEQ ID NO: 6) containing a VLA-4 binding domain and a heparin-binding domain, CH-271 (SEQ ID NO: 7) containing a VLA-5 binding domain and a heparin-binding domain, CH-296 (SEQ ID NO: 8) containing a VLA-4 binding domain, a VLA-5 binding domain and a heparin-binding domain, and C-CS1 (SEQ ID NO: 9) containing a VLA-4 binding domain and a VLA-5 binding domain. These polypeptides are described in J. Biochem., Vol. 110, pp. 284-291 (1991), and can be prepared according to the disclosure. CH-296 is commercially available from TAKARA BIO INC. under the name of RetroNectin (registered trademark).

The FN fragment used in the present invention may be also an altered FN fragment that is a polypeptide having the equivalent function to that of the above-described FN fragment containing at least one part of the amino acid sequence of native FN, and consisting of an amino acid sequence altered from the amino acid sequence of a polypeptide constituting the above-described FN fragment by substitution, deletion, insertion or addition of one or several amino acid residues, as long as the desired effect is obtained by the FN fragment. For example, the altered FN fragment may be obtained by deleting one or two type III repeating sequences from C-274 or H-271. Examples of the altered FN fragment include FN fragments described in WO2008/143255. Herein, whether an altered FN fragment has the equivalent function to that of the above-described FN fragment can be determined by examining the cell-adhesive activity and/or heparin-binding activity of the altered FN fragment. Also, the function of an altered FN fragment can be determined to be equivalent to that of the above-described FN fragment when the altered FN fragment has the equivalent fold expansion in "<3> Method of producing a cell population of the present invention" described later or when the proportion of CD4-positive naive T cells and/or CD4-positive central memory T cells contained in the cell population obtained by the present invention is equivalent.

The cell-adhesive activity can be determined by assaying adhesion between an FN fragment (its cell-adhesive domain) used in the present invention and a cell using a known method. Examples of such a method include the method by Williams D. A., et al. described in Nature, Vol. 352, pp. 438-441 (1991). The method comprises measuring the adhesion of a cell to a fragment immobilized on a culture plate. The heparin-binding activity can be determined by assaying binding between an FN fragment (its heparin-binding domain) used in the present invention and heparin using a known method. For example, the binding between the fragment and heparin can be assessed by the same method as the method of Williams D. A., et al., except that heparin, for example, labeled heparin is used in place of a cell.

Use of a recombinant FN fragment in the present invention is preferred from the viewpoint of easy availability and handling, uniform quality, and a safety aspect in which risk of contamination by viruses or the like is low. The molecular weight of the FN fragment used in the present invention is, but not particularly limited to, preferably 1 to 200 kDa, more preferably 5 to 190 kDa, further more preferably 10 to 180 kDa. The molecular weight can be measured by, for example, SDS-polyacrylamide gel electrophoresis. In the present invention, a mixture of two or more different FN fragments as described above can be also used as the ingredient (A).

Hereinafter, each steps of the production method of the present invention will be specifically explained.

The present invention is a method of producing a cell population expressing CD62L and/or CCR7, characterized by including the following steps.

Step (1): removing CD8-positive cells or collecting CD4-positive T cells from a cell population containing T cells; and Step (2): culturing the cell population obtained by the step (1) in the presence of the following (A) and (B), and for the whole period or a partial period during the culture and/or during expansion after the culture, culturing the cell population in the presence of the following (C):

(A) at least one polypeptide selected from the group consisting of fibronectin, fibronectin fragments and their mixtures, (B) a CD3 ligand, or a CD3 ligand and a CD28 ligand, (C) interleukin-4.

As used herein, the above-described (A), (B) and (C) are also referred to as ingredients for culture in the present invention. Also, in some cases, the "(A) at least one polypeptide selected from the group consisting of fibronectin, fibronectin fragments and their mixtures", the "(B) a CD3 ligand, or a CD3 ligand and a CD28 ligand", and the "(C) interleukin-4" are simply referred to as "the ingredient (A)", "the ingredient (B)", and "the ingredient (C)", respectively.

<1> Step (1) of the Present Invention

In the step (1) of the production method of the present invention, a cell population to be provided for culture is prepared by removing CD8-positive T cells or collecting CD4-positive T cells from a cell population containing T cells. The removal of CD8-positive T cells can be carried out using CD8 expressed on the cell surface as a marker. For example, the removal of CD8-positive T cells is carried out by mixing a support such as a bead or a culture vessel on which an anti-CD8 antibody is immobilized with a cell population containing T cells and then removing CD8-positive T cells bound to the support or collecting a population of cells not bound to the support. Preferable examples of a bead on which an anti-CD8 antibody is immobilized include Dynabeads M-450 CD8 (manufactured by Invitrogen), Eligix anti-CD8 mAb coated nickel particles (manufactured by Bio Transplant Inc.), and CliniMACS System (manufactured by Miltenyi Biotec). Hereinafter, in some cases, a cell population obtained by removing CD8-positive T cells from a cell population containing T cells is referred to as "a CD8-depleted cell population".

The collection of CD4-positive T cells can be carried out using CD4 expressed on the cell surface as a marker. For example, the collection of CD4-positive T cells is carried out by mixing a support such as a bead or a culture vessel on which an anti-CD4 antibody is immobilized with a cell population containing T cells and then collecting CD4-positive T cells bound to the support. Preferable examples of the support on which an anti-CD4 antibody is immobilized include CD4 MicroBeads, and CliniMACS System (manufactured by Miltenyi Biotec), and Dynabeads M-450 CD4 (manufactured by Invitrogen).

In the present invention, the CD8-depleted cell population prepared from a population containing T cells, specifically the CD8-depleted cell population which is obtained using PBMC as the population containing T cells contains monocytes, macrophages and the like together with CD4-positive T cells. Thus, the CD8-depleted cell population is different from a cell population consisting of only CD4-positive T cells selected using CD4 expressed on the cell surface as a marker.

Before the step (1) or the step (2) of the present invention, any cell subpopulation having a specific cell phenotype may be collected or removed. For example, T cells may be collected from PBMC and then subjected to the step (1), or hemocyte components other than T cells, such as monocytes and macrophages may be removed from PBMC and then the remainder may be subjected to the step (1). The procedure is not particularly limited, and for example, a suitable marker on the cell surface, such as a CD marker can be used as a marker. The removal of monocytes from PBMC may be carried out using the ability of monocytes to adhere to plastic material, by culturing PBMC transiently on a culture support made of plastic and then collecting non-adherent cells. In addition, any cell subpopulation can be collected or removed, as appropriate depending on the intended use of a cell population to be prepared.

<2> Step (2) of the Present Invention

In the step (2) of the production method of the present invention, the cell population obtained by the step (1) is cultured in the presence of the ingredients (A) and (B), and for the whole period or a partial period during the culture and/or during expansion after the culture, the cell population is cultured in the presence of the ingredient (C).

The step (2) is carried out by stimulating the cell population obtained by the step (1) in the presence of the ingredients (A) and (B) and then expanding the stimulated cell population. In addition, for the whole period or a partial period during the stimulation and/or during expansion after the stimulation, the cell population is cultured in the presence of the ingredient (C).

Examples of the step (2) include the following aspects.

Aspect 1: The cell population obtained by the step (1) is cultured in the presence of the ingredients (A) and (B), while the ingredient (C) coexists for the whole period or a partial period during the culture. The cell population obtained after the culture is further expanded, and the whole or a part of the expansion is carried out in the presence of the ingredient (C).

Aspect 2: The cell population obtained by the step (1) is cultured in the presence of the ingredients (A) and (B) and in the absence of the ingredient (C). The cell population obtained after the culture is further expanded, and the whole or a part of the expansion is carried out in the presence of the ingredient (C).

Aspect 3: The cell population obtained by the step (1) is cultured in the presence of the ingredients (A) and (B), while the ingredient (C) coexists for the whole period or a partial period during the culture. The cell population obtained after the culture is further expanded in the absence of the ingredient (C).

In the step (2), the expansion may be carried out after culturing in the presence of the ingredients (A) and (B), in the same culture vessel that has been used for the culture in the presence of the ingredients (A) and (B), or in a fresh culture vessel, wherein the cell population is transferred into the fresh culture vessel and then diluted with addition of a fresh medium. For the expansion, the presence or absence of the ingredients (A) and (B) is not particularly limited. The expansion may be carried out in the presence of the ingredients (A) and (B), or the expansion may be carried out after removing either the ingredient (A) or the ingredient (B) or both of them. Preferably, the expansion is carried out in the absence of the ingredients (A) and (B).

The step (2) does not mean a combination of culture wherein culture in the presence of only the ingredient (A), culture in the presence of only the ingredient (B), and culture in the presence of only the ingredient (C) are separately carried out.

In the method of producing a cell population of the present invention, the total culture period is preferably 4 to 20 days from the viewpoint of quality of the obtained cell and efficiency of culture. When the total culture period is 4 to 20 days, the obtained cell population is a cell population containing a high proportion of CD4-positive naive T cells and/or CD4-positive central memory T cells, which is very suitable to use in the field of cell therapy. When the total culture period is less than 4 days, the number of cells sufficient for use in general immunotherapy cannot be obtained. In the present invention, the total culture period is more preferably 5 to 18 days, and further more preferably 6 to 16 days, and it is especially preferably 10 to 14 days from the viewpoint of realizing the desired effect of the present invention that realizes high fold expansion to obtain a larger amount of cells.

Accordingly, the step (2) in the present invention is carried out for 4 days or more, preferably for 5 to 18 days, more preferably for 6 to 16 days, after the start of culture. In the step (2), the culture in the presence of the ingredients (A) and (B) is carried out for 1 day or more, preferably for 2 to 5 days, more preferably for 2 to 4 days, after the start of culture. In the step (2), the expansion is carried out for 1 day or more, preferably for 2 to 12 days, more preferably for 2 to 10 days, using the cell population obtained after the culture in the presence of the ingredients (A) and (B). In the step (2), "a partial period" means a period of culture in the presence of the ingredient (C) during culture in the presence of the ingredients (A) and (B) and/or during expansion after the culture in the presence of the ingredients (A) and (B), and it means a period from the start to the middle of the culture and/or the expansion, a period in the culture and/or the expansion, or a period from the middle to the end of the culture and/or the expansion. The partial period may be also repeated two or more times.

The step (2) may be the whole period or a partial period of a process of culturing a cell population to be prepared for use in immunotherapy. When the step (2) is a partial period of the culture process, prior to the step (2), the cell population obtained by the step (1) may be also cultured in a known medium not containing the ingredients (A), (B) and (C), without particular limitation. In such a case, needless to say, the cell population obtained after the culture must become a cell population having substantially the same properties as the cell population obtained by the step (1) has. The step (2) of the present invention is preferably carried out early in the culture process, and it is more preferably carried out at the start of the culture process.

In the present invention, the total concentration of the ingredient (A) in a culture medium is not particularly limited, and for example, it is preferably 0.001 to 500 µg/mL, more preferably 0.01 to 500 µg/mL.

In the present invention, the CD3 ligand of the ingredient (B) is not particularly limited as long as it is a substance having a CD3-binding activity. Examples of the CD3 ligand include an anti-CD3 antibody, and more preferably an anti-CD3 monoclonal antibody, such as OKT3 [J. Immunol., Vol. 124, No. 6, pp. 2708-2713 (1980)]. When the CD3 ligand is used alone as the ingredient (B), the concentration of the ingredient (B) in a culture medium is not particularly limited, and for example, it is preferably 0.001 to 100 µg/mL, more preferably 0.01 to 100 µg/mL of an anti-CD3 monoclonal antibody.

In the present invention, the CD28 ligand of the ingredient (B) is not particularly limited as long as it is a substance having a CD28-binding activity. Examples of the CD28 ligand include an anti-CD28 antibody, B7-1, B7-2 and CD80, and preferably an anti-CD28 monoclonal antibody. When the CD3 ligand and the CD28 ligand are used as the ingredient (B), the concentration of the CD3 ligand and the CD28 ligand in a culture medium is not particularly limited. For example, when an anti-CD3 monoclonal antibody and an anti-CD28 monoclonal antibody are used, the total concentration of both the antibodies is preferably 0.001 to 100 µg/mL, more preferably 0.01 to 100 µg/mL.

The ingredient (A) and/or the ingredient (B) may be dissolved in a medium to make them coexist or may be immobilized onto a suitable solid phase, for example, an instrument (vessel) for cell culture (including an open system and a closed system) such as a petri dish, a flask or a bag, or a support for cell culture such as a bead, a membrane or a glass slide, when they are used. The material of the solid phase is not particularly limited as long as it can be used for cell culture. Immobilization of the ingredient (A) on the solid phase can be carried out, for example, by contacting a solution of the ingredient (A) in a suitable buffer with the solid phase, or can be also carried our according to methods described in WO 97/18318 and WO 00/09168. When an anti-CD3 antibody and an anti-CD28 antibody are used as the ingredient (B), beads (for example, Dynabeads Human T-Activator CD3/CD28, Dynabeads CD3/CD28, or Dynabeads CliniExVivo CD3/CD28 manufactured by Invitrogen) on which the antibodies are immobilized can be also used.

If the ingredient (A) and/or the ingredient (B) is immobilized on the solid phase, after completion of culture, the obtained cell population can be easily separated from the ingredient(s) simply by separating the cells from the solid phase, and thus contamination of the cell population by the ingredient(s) can be prevented. Although the amount of the ingredient to be immobilized on the instrument or the support is not particularly limited as long as the desired effect is obtained, it is selected so that when the instrument or the support is provided for culture, the ratio of the ingredient to a medium is the same as the desired concentration for the case of dissolving the ingredient in the medium.

In the present invention, interleukin-4 of the ingredient (C) may be obtained naturally or synthesized artificially, that is to say, non-natural. When interleukin-4 is synthesized artificially, a fragment thereof, for example a fragment lacking 1-30 amino acids from the N-terminal of interleukin-4 may be used as long as the desired effect of the present invention is obtained. Also, interleukin-4 may be produced by transferring an interleukin-4 gene into the cell population obtained by the step (1) using an expression vector. The total concentration of the ingredient (C) in a culture medium is not particularly limited, and for example, it is preferably 0.001 to 1000 ng/mL, more preferably 0.01 to 100 ng/mL.

A medium used in the method of producing a cell population of the present invention is not particularly limited, and a known medium prepared by mixing components necessary for expansion of T cells can be used. For example, a commercially available medium can be selected appropriately for use in the production method of the present invention. The medium may contain, in addition to its primary components, cytokines, chemokines, suitable proteins or other components. The cytokines mean cytokines other than interleukin-4, and examples thereof include IL-2, IL-7, IL-12, IL-15 and IFN-γ. Preferably, a medium containing IL-2 is used. The concentration of IL-2 in the medium is not particularly limited, and for example, it is preferably 0.01 to $1\times10^5$ U/mL, more preferably 1 to $1\times10^4$ U/mL. The chemokines are not particularly limited as long as they act on T cells and exhibit chemotactic activity. Examples of the chemokines include RANTES, CCL21, MIP1α, MIP1β, CCL19, CXCL12, IP-10, and MIG. In addition, a lymphocyte stimulation factor such as lectin can be also added to the medium.

In addition, serum or plasma may be added to the medium. The amount of serum or plasma to be added to the medium is not particularly limited. For example, the content of serum or plasma in the medium is more than 0 to 20% by volume. The amount of serum or plasma to be used can be changed depending on a stage of culture. For example, serum or plasma can also be used while stepwise decreasing the concentration thereof. The serum or plasma may be self-derived (meaning that the origin is the same as that of a cell to be cultured) or non-self-derived (meaning that the origin is different from that of a cell to be cultured). An isolated serum component such as human serum albumin may be also added to the medium.

The cell number at the start of culture used in the present invention is not particularly limited, and for example, it is preferably 10 to $1\times10^8$ cells/mL, more preferably $1\times10^2$ to $5\times10^7$ cells/mL, further preferably $1\times10^3$ to $2\times10^7$ cells/mL. The culture conditions are not particularly limited, and conditions which are usually used for cell culture can be used. For example, cells can be cultured under the conditions of 37° C. and 5% $CO_2$. A fresh medium may be added to a cell culture solution at a suitable time interval to dilute the cell culture, a medium may be exchanged, or a cell culture instrument may be exchanged.

In the method of producing a cell population of the present invention, an instrument (vessel) for cell culture can be used as an instrument for culture, and examples thereof include a petri dish, a flask, a bag, a large culture reactor, and a bioreactor. As the bag, a $CO_2$ gas-permeable cell culture bag is preferably used. In the case where a large amount of cells are needed, a large culture reactor may be used. Although cell culture can be carried out in either an open system or a closed system, it is preferable to carry out the cell culture in a closed system from the viewpoint of safety of the obtained cell population.

The method of producing a cell population of the present invention can further comprise a step for foreign gene transfer. The "foreign gene" means a gene to be artificially transferred into a cell population as the target of gene transfer, and also includes a gene derived from the same species as that of the origin of the cell population that is the target of gene transfer.

The step for foreign gene transfer can be carried out at any time point in the method of the present invention. For example, a foreign gene may be transferred into a cell population before the step (1), the cell population obtained by the step (1), or the cell population obtained by the step (2). The step for foreign gene transfer may be also carried out simultaneously with the step (2) or in the middle of the step (2).

A means for transferring a foreign gene is not particularly limited, and a suitable means selected from known gene transfer methods can be used. For example, the step for foreign gene transfer can be carried out using a virus vector or without using a virus vector. With respect to details of these means, many literatures have been already published.

The virus vector is not particularly limited, and a known virus vector which is usually used in a gene transfer method, for example, a retrovirus vector, a lentivirus vector, an adenovirus vector, an adeno-associated virus vector, a simian virus vector, a vaccinia virus vector, a sendaivirus vector or the like can be used. Particularly preferred are a retrovirus vector and a lentivirus vector since they can stably integrate a foreign gene in the vector into the chromosomal DNA of a cell into which the vector is transferred. As the virus vector, preferred is a virus vector lacking the replication ability so as not to self-replicate in an infected cell. For gene transfer, a substance for enhancing gene transfer efficiency such as RetroNectin (registered trademark; manufactured by TAKARA BIO INC.) can be also used.

Examples of a gene transfer method without using a virus vector include a method using a carrier such as liposome or ligand-polylysine, a calcium phosphate method, an electroporation method, and a particle gun method. In such a case, a foreign gene incorporated into a plasmid DNA or a linear DNA or RNA is transferred.

The foreign gene to be transferred is not particularly limited, and any gene [a gene encoding an antisense nucleic acid, a siRNA (small interfering RNA) or a ribozyme as well as a gene encoding a protein (e.g. an enzyme, a cytokine, or a receptor)] can be used depending on the immunotherapy or the target disease for which the cell population obtained by the production method of the present invention is used. For example, a gene expressing MazF which is a sequence-specific ribonuclease can be transferred as the foreign gene into a CD4-positive T cell to obtain a CD4-positive T cell having anti-HIV effect (for example, see WO2007/020873 and WO2008/133137). At the same time, a suitable marker gene that makes it possible to select gene-transferred cells, such as an extracellular domain gene of a low affinity nerve growth factor receptor (ΔLNGFR) may be transferred.

The foreign gene may be inserted into a vector, a plasmid or the like so as to express the gene under the control of a suitable promoter. In addition, an enhancer sequence, a terminator sequence, or an intron sequence may be present in the vector.

<3> Method of Producing a Cell Population of the Present Invention

A feature of the production method of the present invention is a high cell growth rate of a cell population in the process of producing the cell population. As used herein, the cell growth rate is also referred to as fold expansion. The cell growth rate is a numerical value showing a rate (-fold) of the cell number increased for a certain culture period, relative to the cell number at the start of culture. Herein, a high cell growth rate means that the cell growth rate of a cell population under the culture conditions of the method of producing a cell population of the present invention (hereinafter, referred to as the culture conditions of the present invention) is higher than the cell growth rate of a cell population cultured in the presence of the ingredients (A) and (B) and in the absence of the ingredient (C) or cultured in the presence of only the ingredient (B) and in the absence of the ingredient (C) (hereinafter, referred to as the case of not using the culture conditions of the present invention). Using the culture conditions of the present invention for 7 days or more from the start of culture, a cell population can be obtained at a cell growth rate preferably at least 5% higher, more preferably at least 10% higher than the case of not using the culture conditions of the present invention.

According to the production method of the present invention, a cell population containing a high proportion of cells expressing CD62L and/or CCR7, namely a cell population containing a high proportion of CD4-positive naive T cells and/or CD4-positive central memory T cells can be obtained. For the purpose of examining a proportion of CD4-positive naive T cells or CD4-positive central memory T cells in the obtained cell population, a cell surface antigen marker can be measured. For example, the CD4-positive naive T cells are CD45RA-positive and CCR7-positive, CD45RA-positive and CD62L-positive, or CXCR4-positive cells. The CD4-positive central memory T cells are CD45RA-negative and CCR7-positive, CD45RA-negative and CD62L-positive, or CXCR4-positive cells. The cell population obtained by the production method of the present invention can be confirmed to be a cell population containing a high proportion of CD4-positive naive T cells and/or CD4-positive central memory T cells by measuring positive rates of these cell surface antigen markers.

The production method of the present invention may further comprise a step of separating CD4-positive naive T cells and/or CD4-positive central memory T cells from the cell population obtained by the above-described method. The separation can be carried out by a known procedure using a cell sorter, magnetic beads, an affinity column or the like.

If necessary, it is also possible to clone a T cell from the cell population obtained by the method of the present invention and to maintain the cloned T cell as a stable T cell line. Also, the cell population obtained by the method of the present invention can be further cultured by a known method to obtain a new cell population.

A cell population containing a further high proportion of CD4-positive naive T cells and/or CD4-positive central memory T cells can be obtained by carrying out the above-described step.

<4> Cell Population Produced by the Present Invention and Its Use

The present invention also provides the cell population produced by the above-described method. The cell population is a cell population containing a high proportion of CD4-positive naive T cells and/or CD4-positive central memory T cells, as described above. That is, the cell population is a cell population containing a high proportion of at least one kind of cell selected from the group consisting of the following (1) to (5):

(1) a CD4-positive, CD45RA-positive and CCR7-positive T cell,
(2) a CD4-positive, CD45RA-positive and CD62L-positive T cell,
(3) a CD4-positive, CD45RA-negative and CCR7-positive T cell,
(4) a CD4-positive, CD45RA-negative and CD62L-positive T cell, and
(5) a CD4-positive and CXCR4-positive T cell; as compared with a cell population obtained by culture in the presence of the ingredients (A) and (B) or the ingredient (B) and in the absence of the ingredient (C).

The cell population contains a high proportion of preferably at least two, more preferably at least three, further preferably at least four, further more preferably all kinds of cells selected from the group consisting of the above-described (1) to (5), from the viewpoint that a higher content of CD4-positive naive T cells and CD4-positive central memory T cells is desired.

The present invention provides a cell population for use in a medicament, and a cell population according for use in manufacture of a medicament. The cell population is a cell population produced by the present invention. A medicament comprising the cell population is suitable to use in immunotherapy. For example, the cell population produced by the present invention as an active ingredient can be mixed with a known organic or inorganic carrier, an excipient or a stabilizer which are suitable for parenteral administration to form an infusion or an injection. The amount of the cell population of the present invention contained in a therapeutic agent, the dose of the therapeutic agent, and various conditions for the therapeutic agent can be determined as appropriate, according to known immunotherapies. For example, the content of the cell population of the present invention in a medicament is not particularly limited, and for example, it is preferably $1 \times 10^3$ to $1 \times 10^{11}$ cells/mL, more preferably $1 \times 10^4$ to $1 \times 10^{10}$ cells/mL, further preferably $1 \times 10^5$ to $1 \times 10^9$ cells/mL. The dose of the medicament of the present invention is not particularly limited, and for example, it is preferably $1 \times 10^6$ to $1 \times 10^{12}$ cells/day, more preferably $5 \times 10^6$ to $5 \times 10^{11}$ cells/day, further preferably $1 \times 10^7$ to $2 \times 10^{11}$ cells/day for an adult human. An immunotherapy with the therapeutic agent can be also used in combination with a drug therapy by administration of a known drug, a radiation therapy, or a therapy by a surgical operation.

Examples of diseases against which administration of the cell population is effective include, but not particularly limited to, cancer, leukemia, a malignant tumor, hepatitis, and infectious diseases [for example, influenza, tuberculosis, HIV (Human Immunodeficiency Virus) infectious disease, AIDS, MRSA infectious disease, VRE infectious disease, and deep mycosis]. In particular, the cell population is effective for treatment of HIV infectious disease and AIDS (acquired immune deficiency syndrome) caused by HIV that infects CD4-positive T cells. In addition, the cell population produced by the method of the present invention can be also utilized in combination with a conventional therapy including prevention of infectious disease after bone marrow transplantation or irradiation, donor lymphocyte infusion for the purpose of remission of relapsed leukemia, anticancer drug treatment, antibody treatment, hyperthermia treatment, and other immunotherapies. Further, when the method of the present invention comprises a step for transfer of a desired foreign gene, the obtained cell population is useful for treatment or prevention of various diseases affected by the expression of the desired foreign gene.

The present invention also provides a therapeutic or prophylactic method for a disease comprising a step of administering an effective amount of the cell population obtained by the above-described method to a subject. The subject means a patient with the above-described disease. Examples of the subject include human and non-human subjects.

As used herein, the effective amount is the amount of the cell population exerting a therapeutic or prophylactic effect when the cell population is administered to the subject, as compared with a subject to which the cell population is not administered. The specific effective amount can be determined as appropriate and vary depending on the dosage form, administration method, purpose of use, age, body weight or symptom of the subject, and the like, and it is preferably similar to the case of the above-described medicament. An administration method is not limited, and for example, the effective amount may be administered by drip infusion, injection or the like, similarly to the case of the above-described medicament.

In addition, the present invention can produce a cell population containing activated CD4-positive T cells by giving stimulation to the cell population obtained by the above-described production method of the present invention with at least one stimulation factor. Thus, the present invention also provides the cell population thus obtained. The cell population containing activated CD4-positive T cells thus obtained can be used as an active ingredient of a medicine, like the cell population containing CD4-positive naive T cells and/or CD4-positive central memory T cells obtained by the above-described production method. As used herein, the stimulation with a stimulation factor is not particularly limited as long as it can activate the cell population obtained by the above-described production method of the present invention. For example, the stimulation can be carried out by culture of the cell population containing CD4-positive naive T cells and/or CD4-positive central memory T cells obtained by the production method of the present invention under the coexistence with the stimulation factor.

As used herein, a cytokine as the stimulation factor is not particularly limited as long as it is not the ingredient (C) and it can act on and activate CD4-positive naive T cells and/or CD4-positive central memory T cells. Examples of the cytokine as the stimulation factor include IL-2, IFN-γ, TGF-β, IL-15, IL-7, IFN-α, IL-12, CD40L, and IL-27. From the viewpoint of enhancement of cellular immunity, examples of the cytokine as the stimulation factor include IL-2, IFN-γ, and IL-12.

As used herein, the production of a cell population means a process including each step for induction (activation), maintenance, and expansion of the cell population, or steps combining these.

EXAMPLES

The present invention will be further specifically explained by reference to the following Examples, to which the present invention is not limited. In the following Examples, in some cases, the term "stimulation" means that a cell is cultured using a culture vessel on which a stimulation factor is immobilized.

Example 1

Expansion of CD8-Deleted Cell Population Using Interleukin-4 (IL-4) and FN Fragment CH-296

(1) Immobilization of Anti-Human CD3 Antibody and CH-296

Onto culture vessels to be used in the following experiments, an anti-human CD3 antibody (OKT3, Janssen Pharmaceutical K.K.) and a FN fragment having the amino acid sequence set forth in SEQ ID NO: 8 [product name: RetroNectin (registered trademark), manufactured by TAKARA BIO INC.; hereinafter, referred to as CH-296] were immobilized. Specifically, an ACD-A solution (manufactured by TERUMO CORPORATION) containing the anti-human CD3 antibody at a final concentration of 5 μg/mL and CH-296 at a final concentration of 25 μg/mL was added onto a 12-well cell culture plate (Falcon) at 0.4 mL/well, and then the plate was incubated at 37° C. for 5 hours. Then, the ACD-A solution containing CH-296 was removed from each well by suction. Each well was washed twice with 0.5 mL of a GT-T503 medium (manufactured by TAKARA BIO INC.). The plate thus prepared (hereinafter, referred to as an anti-human CD3 antibody/CH-296 immobilized plate) was used in each experiment.

(2) Preparation of CD8-Depleted Cell Population

A human peripheral blood mononuclear cell (PBMC) was prepared according to a conventional method from a healthy human donor after obtaining informed consent. PBMC was suspended at $1 \times 10^7$ cells/mL in PBS containing 2 mM EDTA and 0.1% BSA (hereinafter, referred to as Buffer 1). Thereafter, CD8-positive selection beads (Dynabeads M-450 CD8: manufactured by Invitrogen) washed with Buffer 1 were added at $2 \times 10^7$ beads per $1 \times 10^7$ cells of PBMC. After gently stirring at 4° C. for 30 minutes with a rotator, the cell suspension containing the beads was allowed to stand still on a magnetic separator MPC-15 (manufactured by Dynal) for 2 to 3 minutes to collect beads-unbound cells (hereinafter, referred to as a CD8-depleted cell population). The collected CD8-depleted cell population was centrifuged at 500×g for 5 minutes, and then suspended at $4 \times 10^5$ cells/mL in a GT-T503 medium (manufactured by TAKARA BIO INC.) containing 1% human autologous plasma, 100 IU/mL of IL-2 (Proleukin, manufactured by Nipro Corporation), 0.2% human serum albumin (manufactured by Baxter), 2.5 µg/mL of fungizone (manufactured by Bristol-Myers Squibb) and 50 U/mL of penicillin/streptomycin (manufactured by Invitrogen) (hereinafter, referred to as GT-T503CM).

(3) Expansion of Cell Population

The CD8-depleted cell population as prepared in Example 1-(2) was cultured. The culture was carried out under the condition of using GT-T503CM containing 10 ng/mL of IL-4 for the whole culture period (D0-12 group), or the condition of using GT-T503CM containing IL-4 at the same concentration as described above from day 4 of culture (D4-12 group). As a negative control, the CD8-depleted cell population was cultured without addition of IL-4 (Non-addition group).

First, the CD8-depleted cell population as prepared in Example 1-(2) was added at 1.3 mL/well onto the anti-human CD3 antibody/CH-296 immobilized plate as prepared in Example 1-(1). Further, human recombinant IL-4 (manufactured by R&D systems; a 10 µg/mL solution in PBS containing 0.1% HSA) was diluted with GT-T503CM so as to be 20 ng/mL, and added to the plate at 1.3 mL/well (final concentration of IL-4: 10 ng/mL). For D4-12 group and Non-addition group, 1.3 mL of GT-T503CM was added to the plate, and the plate was incubated at 37° C. in a 5% CO$_2$ incubator (Day 0 of culture).

On the 4th day of culture, the number of cells in each test group was counted by a trypan blue staining method. For further dilution culture, the cells were suspended in GT-T503CM at $1 \times 10^5$ cells/mL, and added at 4 mL/well to a 12-well cell culture plate (Falcon) on which nothing was immobilized. At this time, in D0-12 group and D4-12 group, the dilution culture was carried out using GT-T503CM containing 10 ng/mL of IL-4. On day 7 of culture, the cells in D0-12 group and D4-12 group were diluted 5-fold with GT-T503CM containing IL-4 at the same concentration as described above, and the cells in Non-addition group were diluted 5-fold with GT-T503CM not containing IL-4. Each of these dilutions was added at 4 mL/well to a 12-well cell culture plate (Falcon) on which nothing was immobilized, and cultured. On the 11th day of culture, dilution culture was carried out in the same manner as in the 7th day of culture, except that the cells were diluted 2-fold. Fold expansion on the 12th day from the start of culture is shown in Table 1. The fold expansion was a ratio of the cell number on day 12 of culture to the cell number at the start of culture when the cell number was counted by a trypan blue staining method and the cell number at the start of culture was defined as 1.

TABLE 1

| Test group | Fold expansion (-fold) |
| --- | --- |
| Non-addition group | 283.3 |
| D0-12 group | 669.5 |
| D4-12 group | 407.6 |

As seen in Table 1, in the groups with addition of IL-4, higher fold expansion was achieved as compared with Non-addition group. Thus, it was demonstrated that use of IL-4 increased fold expansion in culture of a CD4-positive T cell with an anti-human CD3 antibody and CH-296. It was also demonstrated that higher fold expansion was achieved when an IL-4 addition medium was used for the whole culture period, as compared with use of an IL-4 addition medium from day 4 of culture.

(4) Analysis of Cell Surface Marker

The cell population on day 12 of culture obtained in Example 1-(3) was washed with PBS containing 0.1% bovine serum albumin (hereinafter, referred to as 0.1% BSA/PBS). The cell population was suspended in 0.1% BSA/PBS. To the cell suspension were added as an antibody reaction solution 1, an antibody solution containing an FITC-labeled mouse anti-human CD8 antibody (manufactured by Becton Dickinson), an RD1-labeled mouse anti-human CD45RA antibody (manufactured by BECKMAN COULTER), a PerCP-labeled mouse anti-human CD3 antibody (manufactured by Becton Dickinson), a PE-Cy7-labeled mouse anti-human CD62L antibody (manufactured by eBioscience), and an APC-Cy7-labeled mouse anti-human CD4 antibody (manufactured by Becton Dickinson), and further as an antibody reaction solution 2, an antibody solution containing an FITC-labeled mouse anti-human CD8 antibody, a PE-labeled mouse anti-human CXCR4 antibody (manufactured by Becton Dickinson), a PerCP-labeled mouse anti-human CD3 antibody, and an APC-Cy7-labeled mouse anti-human CD4 antibody, to perform the antibody reaction. Thereafter, the cell population was washed twice with 0.1% BSA/PBS, and again suspended in 0.1% BSA/PBS. The cell population thus obtained was subjected to flow cytometry (FACS CantoII: manufactured by Becton Dickinson). The rate of each cell surface marker contained in CD3-positive CD4-positive cells of each cell population was calculated. The CD3-positive rate in the all cells was 94% or more in the all test groups. Results are shown in Table 2.

TABLE 2

| Test group | CD45RA+ CD62L+ rate (%) | CD45RA− CD62L+ rate (%) | CD62L+ rate (%) | CXCR4+ rate (%) |
| --- | --- | --- | --- | --- |
| Non-addition group | 33.4 | 25.7 | 59.1 | 51.3 |
| D0-12 | 46.4 | 30.4 | 76.8 | 73.7 |
| D4-12 | 46.3 | 26.6 | 72.9 | 80.1 |

As seen in Table 2, in the groups with addition of IL-4, cell populations having a higher CD45RA+CD62L+ rate, a higher CD45RA− CD62L+ rate, and a higher CXCR4+ rate were obtained as compared with Non-addition group. The cell surface marker of naive T cells is CD45RA+CD62L+, the cell surface marker of central memory T cells is CD45RA− CD62L+, and the cell surface marker of naive T cells and central memory T cells is CXCR4. Thus, it was demonstrated that a cell population containing a high proportion of CD4-positive naive T cells and CD4-positive central memory T cells could be efficiently obtained by adding IL-4 when a CD4-positive T cell was cultured with an anti-human CD3 antibody and CH-296.

Example 2

Expansion of CD4-Positive T Cell Population Using IL-4 and FN Fragment CH-296

(1) Immobilization of Anti-Human CD3 Antibody and CH-296

In the same manner in Example 1-(1), only an anti-human CD3 antibody was immobilized on a 12-well cell culture plate (Falcon), and washed. The plate thus prepared (hereinafter, referred to as an anti-human CD3 antibody-immobilized plate) was used in each experiment. Further, an anti-human CD3 antibody/CH-296 immobilized plate was also prepared and used in each experiment.

(2) Preparation of CD4-Positive T Cell Population

PBMCs were prepared according to a conventional method from healthy human donors TK19 and TK29 after obtaining informed consent. The PBMCs were each suspended in GT-T503CM containing 10 μg/mL of DNase. Thereafter, the cell suspension was centrifuged at 500×g for 5 minutes, and supernatant was removed. The cell population thus obtained was suspended in Buffer 1 at $1 \times 10^7$ cells/80 μL. To the cell suspension, human CD4 MicroBeads (manufactured by Miltenyi Biotec) were added in an amount of 20 μL per $1 \times 10^7$ cells, and left at 4° C. for 15 minutes. Then, to the cell suspension, Buffer 1 was added in an amount of 1.8 mL per $1 \times 10^7$ cells. The cell suspension was centrifuged at 300×g for 10 minutes, and supernatant was removed. The cells were suspended in 500 μL of Buffer 1. MACS separation LS columns (manufactured by Miltenyi Biotec) were set in a VarioMACS separator (manufactured by Miltenyi Biotec). After 3 mL of Buffer 1 was allowed to pass through the columns, the above-described cell suspension was added on the columns. After the columns were washed thrice with 5 mL of Buffer 1, the columns were removed from the separator, 5 mL of Buffer 1 was added to the columns, and a cell solution was extruded by a syringe. Thus a CD4-positive T cell population was obtained.

(3) Expansion of Cell Population

The CD4-positive T cell population as prepared in Example 2-(2) was cultured. The culture was carried out in GT-T503CM containing 10 ng/mL of IL-4 for the whole culture period under the condition of stimulating with an anti-human CD3 antibody alone (anti-CD3 stimulation group), or the condition of stimulating with an anti-human CD3 antibody and CH-296 (anti-CD3/CH-296 stimulation group). As a negative control, the CD4-positive T cell population was cultured without addition of IL-4 (Non-addition group).

First, the CD4-positive T cell population as prepared in Example 2-(2) was centrifuged to remove supernatant, and suspended at $2 \times 10^5$ cells/mL in GT-T503CM containing IL-4 or GT-T503CM not containing IL-4. The cell population thus prepared was added at 2.6 mL/well onto the anti-human CD3 antibody-immobilized plate or the anti-human CD3 antibody/CH-296 immobilized plate as prepared in Example 2-(1). These plates were incubated at 37° C. in a 5% $CO_2$ incubator (Day 0 of culture).

On the 4th day of culture, the number of cells in each test group was counted by a trypan blue staining method. For further dilution culture, the cells in the all test groups were suspended at $1 \times 10^5$ cells/mL in GT-T503CM containing IL-4 or GT-T503CM not containing IL-4, and added at 4 mL/well to a 12-well cell culture plate (Falcon) on which nothing was immobilized. On day 7 of culture, the cells were diluted 4-fold with each culture medium, added at 4 mL/well to a 12-well cell culture plate (Falcon) on which nothing was immobilized, and cultured. On the 10th day of culture, dilution culture was carried out in the same manner as in the 7th day of culture, except that the cells were diluted 2-fold. Fold expansion on the 12th day from the start of culture is shown in Table 3. The fold expansion was a ratio of the cell number on day 12 of culture to the cell number at the start of culture when the cell number was counted by a trypan blue staining method and the cell number at the start of culture was defined as 1. In the table, "+" represents a test group in which GT-T503CM containing IL-4 was used, and "−" represents Non-addition group.

TABLE 3

| Donor | Test group | IL-4 | Fold expansion (-fold) |
|---|---|---|---|
| TK19 | anti-CD3 | − | 282.7 |
| | stimulation group | + | 425.1 |
| | anti-CD3/CH-296 | − | 437.0 |
| | stimulation group | + | 1336.1 |
| TK29 | anti-CD3 | − | 120.1 |
| | stimulation group | + | 114.0 |
| | anti-CD3/CH-296 | − | 186.8 |
| | stimulation group | + | 487.4 |

As seen in Table 3, in the anti-CD3/CH-296 stimulation groups, remarkably higher fold expansion was achieved as compared with Non-addition group. In the anti-CD3 stimulation groups, the growth-stimulating effect was not found depending on the donors. Thus, it was demonstrated that fold expansion of a CD4-positive T cell population with addition of IL-4 was remarkably increased by stimulation with an anti-human CD3 antibody and CH-296.

(4) Analysis of Cell Surface Marker

The cell population on day 12 of culture obtained in Example 2-(3) was washed with 0.1% BSA/PBS. The cells were suspended in 0.1% BSA/PBS. To the cell suspension was added an antibody solution containing an FITC-labeled mouse anti-human CD8 antibody, an RD1-labeled mouse anti-human CD45RA antibody, a PerCP-labeled mouse anti-human CD3 antibody, a PE-Cy7-labeled mouse anti-human CD62L antibody, and an APC-Cy7-labeled mouse anti-human CD4 antibody, to perform the antibody reaction. Thereafter, the cells were washed twice with 0.1% BSA/PBS, and again suspended in 0.1% BSA/PBS. The cell suspension thus obtained was subjected to flow cytometry. The rate of each cell surface marker contained in CD3-positive CD4-positive cells of each cell population was calculated. Results are shown in Table 4 and Table 5. In the tables, "+" represents a test group in which GT-T503CM containing IL-4 was used, and "−" represents Non-addition group.

TABLE 4

| Donor | Test group | IL-4 | CD45RA+ CCR7+ rate (%) | CD45RA− CCR7+ rate (%) | CCR7+ rate (%) |
|---|---|---|---|---|---|
| TK19 | anti-CD3 | − | 3.1 | 7.9 | 11.0 |
| | stimulation group | + | 5.5 | 6.4 | 11.9 |

TABLE 4-continued

| Donor | Test group | IL-4 | CD45RA+ CCR7+ rate (%) | CD45RA− CCR7+ rate (%) | CCR7+ rate (%) |
|---|---|---|---|---|---|
| | anti-CD3/CH-296 | − | 14.7 | 7.7 | 22.4 |
| | stimulation group | + | 17.2 | 9.7 | 26.9 |
| TK29 | anti-CD3 | − | 1.1 | 7.8 | 8.9 |
| | stimulation group | + | 2.6 | 14.5 | 17.1 |
| | anti-CD3/CH-296 | − | 4.9 | 8.5 | 13.4 |
| | stimulation group | + | 12.6 | 9.8 | 22.4 |

TABLE 5

| Donor | Test group | IL-4 | CD45RA+ CD62L+ rate (%) | CD45RA− CD62L+ rate (%) | CD62L+ rate (%) |
|---|---|---|---|---|---|
| TK19 | anti-CD3 | − | 15.8 | 19.8 | 35.6 |
| | stimulation group | + | 25.7 | 30.5 | 56.2 |
| | anti-CD3/CH-296 | − | 35.6 | 18.3 | 53.9 |
| | stimulation group | + | 37.8 | 34.8 | 72.6 |
| TK29 | anti-CD3 | − | 9.7 | 39.4 | 49.1 |
| | stimulation group | + | 11.9 | 41.1 | 53.0 |
| | anti-CD3/CH-296 | − | 14.0 | 31.5 | 45.5 |
| | stimulation group | + | 30.8 | 38.9 | 69.7 |

As seen in Table 4 and Table 5, in the groups with addition of IL-4, cell populations having a higher CCR7+ rate, a higher CD45RA+ CCR7+ rate, a higher CD45RA− CCR7+ rate, a higher CD62L+ rate, a higher CD45RA+ CD62L+ rate, and a higher CD45RA− CD62L+ rate were obtained as compared with Non-addition group. These positive cell rates were higher in the anti-CD3/CH-296 stimulation groups than the anti-CD3 stimulation groups. When an IL-4 addition medium was used for culture, their positive cell rates were further increased. The cell surface marker of naive T cells is CD45RA+CCR7+, and the cell surface marker of central memory T cells is CD45RA− CCR7+. Thus, it was demonstrated that a cell population containing CD4-positive naive T cells and CD4-positive central memory T cells could be obtained with high efficiency by adding IL-4 when a CD4-positive T cell population was cultured with an anti-human CD3 antibody and CH-296.

Example 3

Expansion of CD4-Positive T Cell Population into which ΔLNGFR and MazF Genes are Transferred, Using IL-4 and FN Fragment CH-296

(1) Preparation of Retroviral Vector Carrying ΔLNGFR and MazF Genes

A retroviral vector carrying ΔLNGFR and MazF genes was prepared as described in Examples 1 and 2 of WO 2008/133137. Specifically, a recombinant retroviral vector plasmid pMT-MFR-PL2 into which an HIV LTR-MazF cassette was inserted in the reverse direction to transcription of the retroviral vector genome and a human ΔLNGFR was inserted downstream of a human PGK promoter in the forward direction was prepared, and used to prepare an ecotropic MT-MFR-PL2 virus. Then, a GaLV retrovirus packaging cell PG13 was infected with the ecotropic MT-MFR-PL2 virus, and a virus producer cell with high titer was cloned to establish a retroviral vector producer cell line PG13/MT-MFR-PL2. Furthermore, the producer cell was used to obtain a GaLV/MT-MFR-PL2 virus solution by a conventional method.

(2) Immobilization of Anti-Human CD3 Antibody and CH-296

In the same manner in Example 1-(1), an anti-human CD3 antibody/CH-296 immobilized plate was prepared, and used in each experiment.

(3) Preparation of CD4-Positive T Cell Population

In the same manner as in Example 2-(2), a CD4-positive T cell population was obtained from a healthy human donor after obtaining informed consent.

(4) Gene Transfer and Expansion

The cell population as prepared in Example 3-(3) was centrifuged to remove supernatant, and then suspended at $2\times10^5$ cells/mL in GT-T503CM containing IL-4 or GT-T503CM not containing IL-4. The cells thus prepared were added at 2.6 mL/well onto the anti-human CD3 antibody/CH-296 immobilized plate as prepared in Example 3-(2). The plate was incubated at 37° C. in a 5% $CO_2$ incubator (Day 0 of culture).

On the 4th day of culture, the number of cells in each test group was counted by a trypan blue staining method. The cells were adjusted with GT-T503CM containing IL-4 or GT-T503CM not containing IL-4 so as to be $1\times10^5$ cells/mL. Next, the GaLV/MT-MFR-PL2 virus solution as prepared in Example 3-(1) was diluted 2-fold with GT-T503, added at 0.5 mL/well to a 12-well cell culture plate (Falcon) on which CH-296 was previously immobilized (hereinafter, referred to as a CH-296 immobilized plate), and then centrifuged at 32° C. and 2000×g for 2 hours, thereby the retrovirus vector was bound to the plate. Then, the supernatant was removed, and the plate was washed twice with 1 mL/well of PBS containing 1.5% HSA. To the plate was added 1 mL/well of the cell suspension obtained on the 4th day of culture and adjusted so as to be $1\times10^5$ cells/mL. The plate was incubated at 37° C. in a 5% $CO_2$ incubator (Day 0 of culture), and thereby the cells were infected with the retrovirus vector. On the 6th day of culture, the cells were diluted 5-fold, added at 4 mL/well to a 12-well cell culture plate on which nothing was immobilized, and cultured. On the 8th day of culture, dilution culture was carried out in the same manner as in the 6th day of culture, except that the cells were diluted 4-fold. Fold expansion on the 12th day from the start of culture is shown in Table 6. The fold expansion was a ratio of the cell number on day 12 of culture to the cell number at the start of culture when the cell number was counted by a trypan blue staining method and the cell number at the start of culture was defined as 1. In the table, "+" represents a test group in which GT-T503CM containing IL-4 was used, and "−" represents Non-addition group.

TABLE 6

| IL-4 | Gene transfer | Fold expansion (-fold) |
|---|---|---|
| − | Without gene transfer | 156.4 |
| + | Without gene transfer | 364.7 |
| − | With gene transfer | 128.0 |
| + | With gene transfer | 330.1 |

As seen in Table 6, it was demonstrated that even when gene transfer with a retrovirus vector was carried out, higher fold expansion could be achieved by using an IL-4 addition medium, as compared with Non-addition group.

(5) Gene Transfer Efficiency and Analysis of Cell Surface Marker

The cell population on day 12 of culture obtained in Example 3-(4) was washed with 0.1% BSA/PBS. The cells were suspended in 0.1% BSA/PBS. To the cell suspension were added as an antibody reaction solution 1, an antibody solution containing an FITC-labeled mouse anti-human CCR7 (manufactured by R&D systems), an RD1-labeled mouse anti-human CD45RA antibody, a PerCP-labeled mouse anti-human CD3 antibody, a PE-Cy7-labeled mouse anti-human CD62L antibody, an APC-labeled mouse anti-human LNGFR antibody (manufactured by Miltenyi Biotec) and APC-Cy7-labeled mouse anti-human CD4 antibody, and further as an antibody reaction solution 2, an antibody solution containing a PE-labeled mouse anti-human CXCR4 antibody, a PerCP-labeled mouse anti-human CD3 antibody and an APC-Cy7-labeled mouse anti-human CD4 antibody, to perform the antibody reaction. Thereafter, the cells were washed twice with 0.1% BSA/PBS, and again suspended in 0.1% BSA/PBS. The cell suspension thus obtained was subjected to flow cytometry. The rate of each cell surface marker contained in CD3-positive CD4-positive cells of each cell population was calculated. Results are shown in Tables 7 to 10. In the tables, "+" represents the case of using GT-T503CM containing IL-4, and "−" represents the case of non-addition.

TABLE 7

| IL-4 | Gene transfer | ΔLNGFR-positive rate (%) |
|---|---|---|
| − | Without gene transfer | 0.6 |
| + | Without gene transfer | 0.7 |
| − | With gene transfer | 14.5 |
| + | With gene transfer | 14.7 |

TABLE 8

| IL-4 | Gene transfer | CD45RA+ CCR7+ rate (%) | CD45RA− CCR7+ rate (%) | CCR7+ rate (%) |
|---|---|---|---|---|
| − | Without gene transfer | 23.5 | 6.7 | 30.2 |
| + | Without gene transfer | 30.3 | 9.5 | 39.8 |
| − | With gene transfer | 24.3 | 7.9 | 32.2 |
| + | With gene transfer | 32.7 | 9.7 | 42.4 |

TABLE 9

| IL-4 | Gene transfer | CD45RA+ CD62L+ rate (%) | CD45RA− CD62L+ rate (%) | CD62L+ rate (%) |
|---|---|---|---|---|
| − | Without gene transfer | 35.1 | 33.4 | 68.5 |
| + | Without gene transfer | 47.3 | 42.0 | 89.3 |
| − | With gene transfer | 34.4 | 30.5 | 64.9 |
| + | With gene transfer | 51.4 | 37.6 | 89.0 |

TABLE 10

| IL-4 | Gene transfer | CXCR4− positive rate (%) |
|---|---|---|
| − | Without gene transfer | 60.2 |
| + | Without gene transfer | 70.7 |
| − | With gene transfer | 62.9 |
| + | With gene transfer | 77.9 |

As seen in Tables 7 to 10, in the IL-4 addition test groups, there was no negative effect on gene transfer efficiency in the process for preparing a gene-transferred cell using a retrovirus vector, and furthermore, cell populations having a high CCR7+ rate, a high CD45RA+ CCR7+ rate, a high CD45RA− CCR7+ rate, a high CD62L+ rate, a high CD45RA+ CD62L+ rate, a high CD45RA− CD62L+ rate, and a high CXCR4+ rate were obtained. Thus, it was demonstrated that a cell population containing gene-transferred CD4-positive naive T cells and gene-transferred CD4-positive central memory T cells could be grown with high efficiency by using IL-4 even when a gene-transferred CD4-positive T cell was cultured with an anti-human CD3 antibody and CH-296.

INDUSTRIAL APPLICABILITY

According to the present invention, a method of producing with high fold expansion a cell population expressing CD62L and/or CCR7, namely, a cell population containing a high proportion of CD4-positive naive T cells and/or CD4-positive central memory T cells is provided. The cell population obtained by the production method is very useful for treating diseases by cell-based immunotherapy and gene therapy.

SEQUENCE LISTING FREE TEXT

SEQ ID NO:1; Partial region of fibronectin named CS-1.
SEQ ID NO:2; Partial region of fibronectin named III-10.
SEQ ID NO:3; Partial region of fibronectin named RGDS.
SEQ ID NO:4; Fibronectin fragment named C-274.
SEQ ID NO:5; Fibronectin fragment named H-271.
SEQ ID NO:6; Fibronectin fragment named H-296.
SEQ ID NO:7; Fibronectin fragment named CH-271.
SEQ ID NO:8; Fibronectin fragment named CH-296.
SEQ ID NO:9; Fibronectin fragment named C-CS1.

The invention claimed is:

1. A method of producing CD4-positive naïve T cells and/or CD4-positive central memory T cells expressing CD62L and/or CCR7, the method comprising the following steps:
  (1) removing CD8-positive T cells or collecting CD4-positive T cells from a cell population containing T cells; and
  (2) culturing the cell population obtained by the step (1) in the presence of the following (A) and (B), and for the whole period or a partial period during the culture and/or during expansion after the culture, culturing the cell population in the presence of the following (C):
  (A) at least one polypeptide selected from the group consisting of fibronectin, fibronectin fragments and their mixtures,
  (B) a CD3 ligand, or a CD3 ligand and a CD28 ligand,
  (C) interleukin-4 in an amount of 0.01 to 100 ng/ml.

2. The method according to claim 1, wherein the step (2) is a step of culturing the cell population in the presence of (A) and (B) and in the presence of (C), and then expanding the obtained cell population in the presence of (C).

3. The method according to claim 1, wherein the step (2) is a step of culturing the cell population in the presence of (A) and (B) and in the absence of (C), and then expanding the obtained cell population in the presence of (C).

4. The method according to claim 1, wherein the step (2) is a step of culturing the cell population in the presence of (A) and (B) and in the presence of (C), and then expanding the obtained cell population in the absence of (C).

5. The method according to claim 1, further comprising a step for foreign gene transfer.

6. The method according to claim 1, wherein the cell population containing T cells in step (1) is peripheral blood mononuclear cells (PBMC).

\* \* \* \* \*